US00PP32496P2

(12) United States Plant Patent
Vitten et al.

(10) Patent No.: US PP32,496 P2
(45) Date of Patent: Nov. 24, 2020

(54) RASPBERRY PLANT NAMED 'DRISRASPFIFTEEN'

(50) Latin Name: ***Rubus idaeus* L.**
Varietal Denomination: DrisRaspFifteen

(71) Applicant: Driscoll's, Inc., Watsonville, CA (US)

(72) Inventors: Matthias D. Vitten, Watsonville, CA (US); Moises D. Gonzalez, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/501,853

(22) Filed: Jun. 19, 2019

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204, 203
CPC ..... A01H 5/0887
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP7,528 | P | 5/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| PP27,644 | P3 | 2/2017 | Hamilton et al. |
| PP28,775 | P2 | 12/2017 | Hamilton et al. |
| PP28,856 | P3 | 1/2018 | Vitten et al. |
| PP29,402 | P2 | 6/2018 | Vitten et al. |
| PP30,577 | P2 | 6/2019 | Vitten et al. |
| PP30,733 | P2 | 7/2019 | Hamilton et al. |

OTHER PUBLICATIONS

Cousineau et al., "Use of Isoenzyme Analysis to Characterize Raspberry Cultivars and Detect Cultivar Mislabeling", HortScience vol. 27, No. 9, Sep. 1992, pp. 1023-1025.
Hamilton et al., Unpublished U.S. Appl. No. 16/350,839, filed Jan. 22, 2019, titled "Raspberry Plant Variety Named 'DrisRaspFourteen'".
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Kent L Bell
(74) *Attorney, Agent, or Firm* — Morrison & Foerster LLP

(57) ABSTRACT

A new and distinct variety of raspberry plant named 'DrisRaspFifteen', particularly selected for its primocane and floricane yield, fruit size, fruit flavor, and shelf life, is disclosed.

4 Drawing Sheets

Latin name:
Botanical classification: *Rubus idaeus* L.
Varietal denomination: The varietal denomination of the claimed variety of raspberry plant is 'DrisRaspFifteen'.

BACKGROUND OF THE INVENTION

Raspberries are the edible fruit of a multitude of plant species in the genus *Rubus* of the rose family. Most raspberry species are in the subgenus Idaeobatus. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L.), which has been denominated as 'DrisRaspFifteen'.

Raspberry plant variety 'DrisRaspFifteen' was discovered in Ventura County, Calif. in February of 2013 and originated from a cross between the proprietary female parent 'RD335.8' (unpatented) and the proprietary male parent 'Z367.1' (unpatented). The original seedling of the new variety was first asexually propagated in Santa Cruz County, Calif. via cuttings in May of 2013.

'DrisRaspFifteen' was subsequently asexually propagated via root cuttings, and underwent further testing in Santa Cruz County, Calif. for three years (2015 to 2018). The present variety has been found to be stable and reproduce true to type through successive asexual propagations via root cuttings.

'DrisRaspFifteen' exhibits the following distinguishing characteristics over similar raspberry varieties when grown under normal horticultural practices in Santa Cruz County, Calif.:

1. Arching growth habit;
2. Free relative position of lateral leaflets; and
3. Conical fruit shape.

'DrisRaspFifteen' was particularly selected for its primocane and floricane yield, fruit size, fruit flavor, and shelf life.

BRIEF DESCRIPTION OF THE DRAWINGS

This new raspberry plant is illustrated by the accompanying photographs. The colors shown are as true as can be reasonably obtained by conventional photographic procedures. The photographs are of plants that are from one to two years old.

DETAILED BOTANICAL DESCRIPTION

Figure 1:
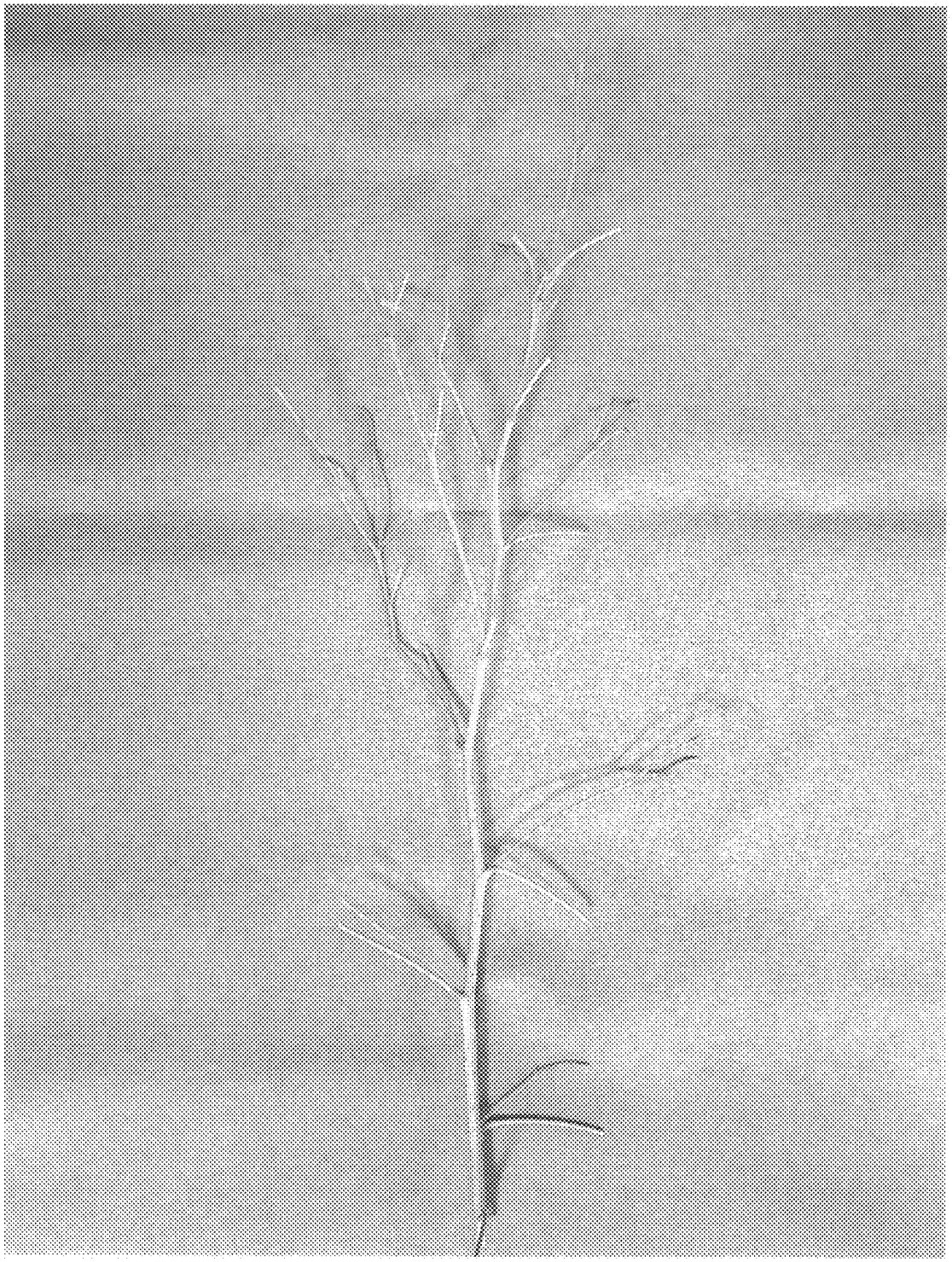
FIG. 1 illustrates a section of cane of raspberry variety 'DrisRaspFifteen'.
Figures 2A, 2B:
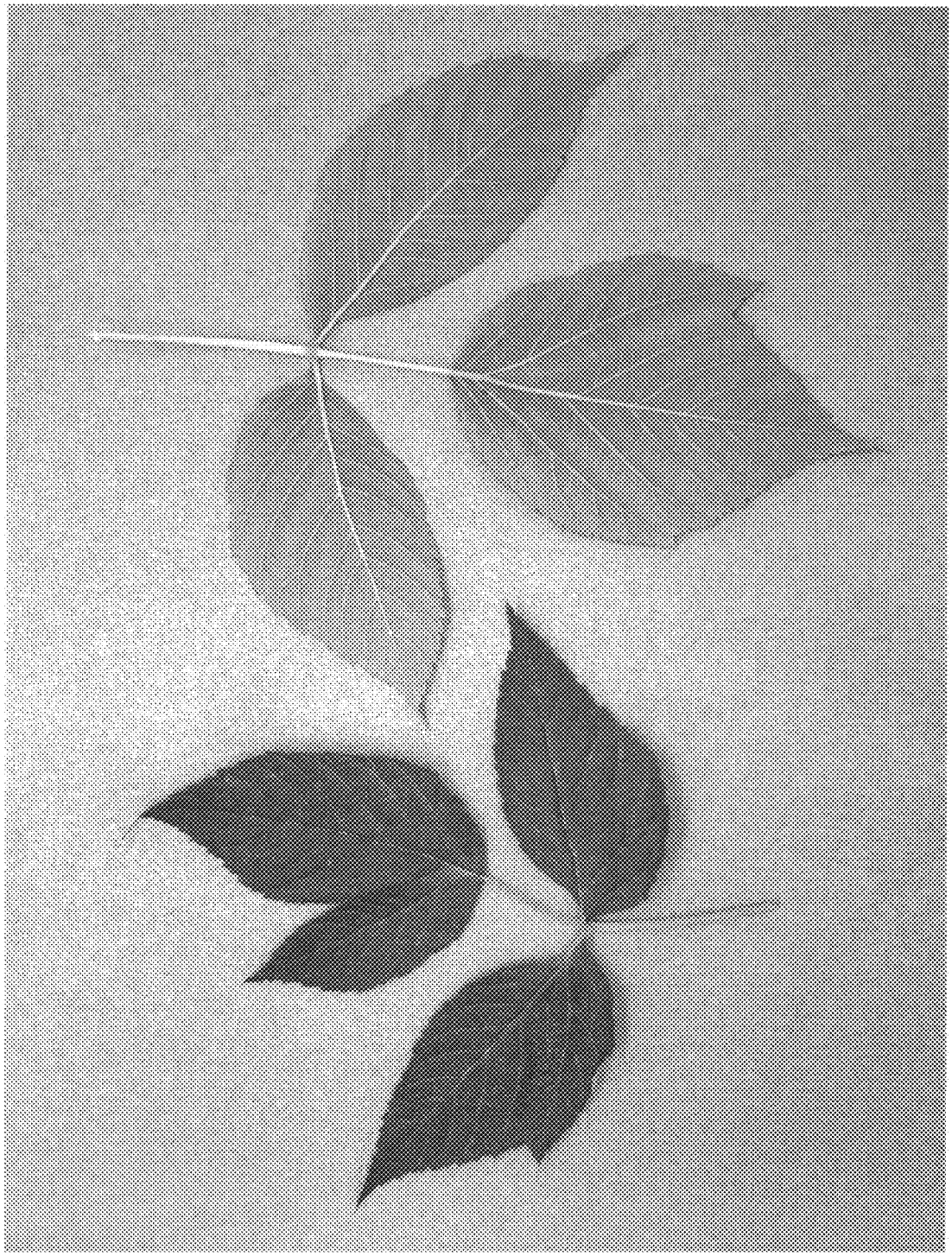
FIG. 2A and FIG. 2B illustrate both the upper surface (FIG. 2A) and the lower surface (FIG. 2B) of leaves of raspberry variety 'DrisRaspFifteen'.
Figure 3:
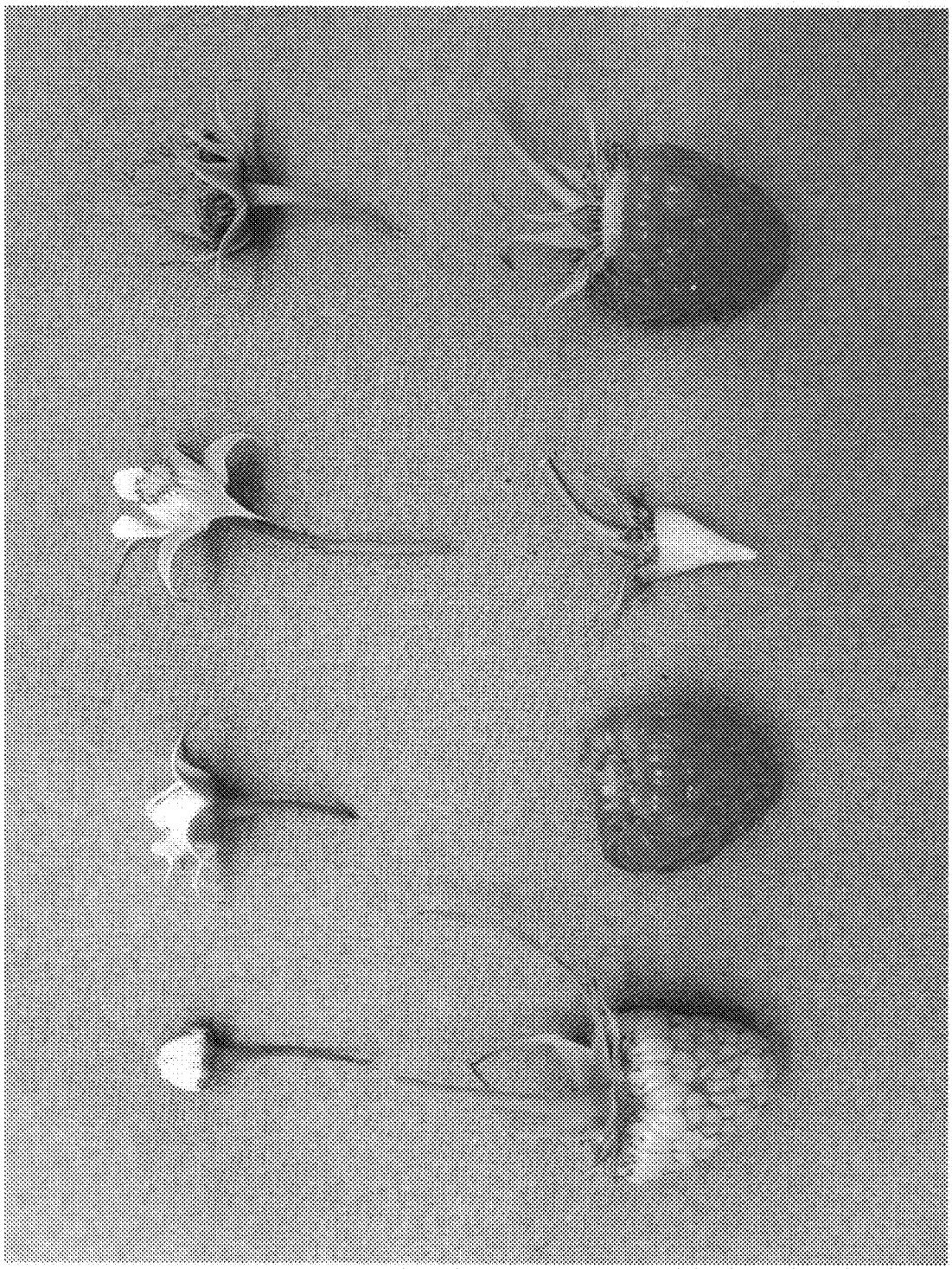
FIG. 3 illustrates fruit of raspberry variety 'DrisRaspFifteen' at various stages of development.
Figure 4:
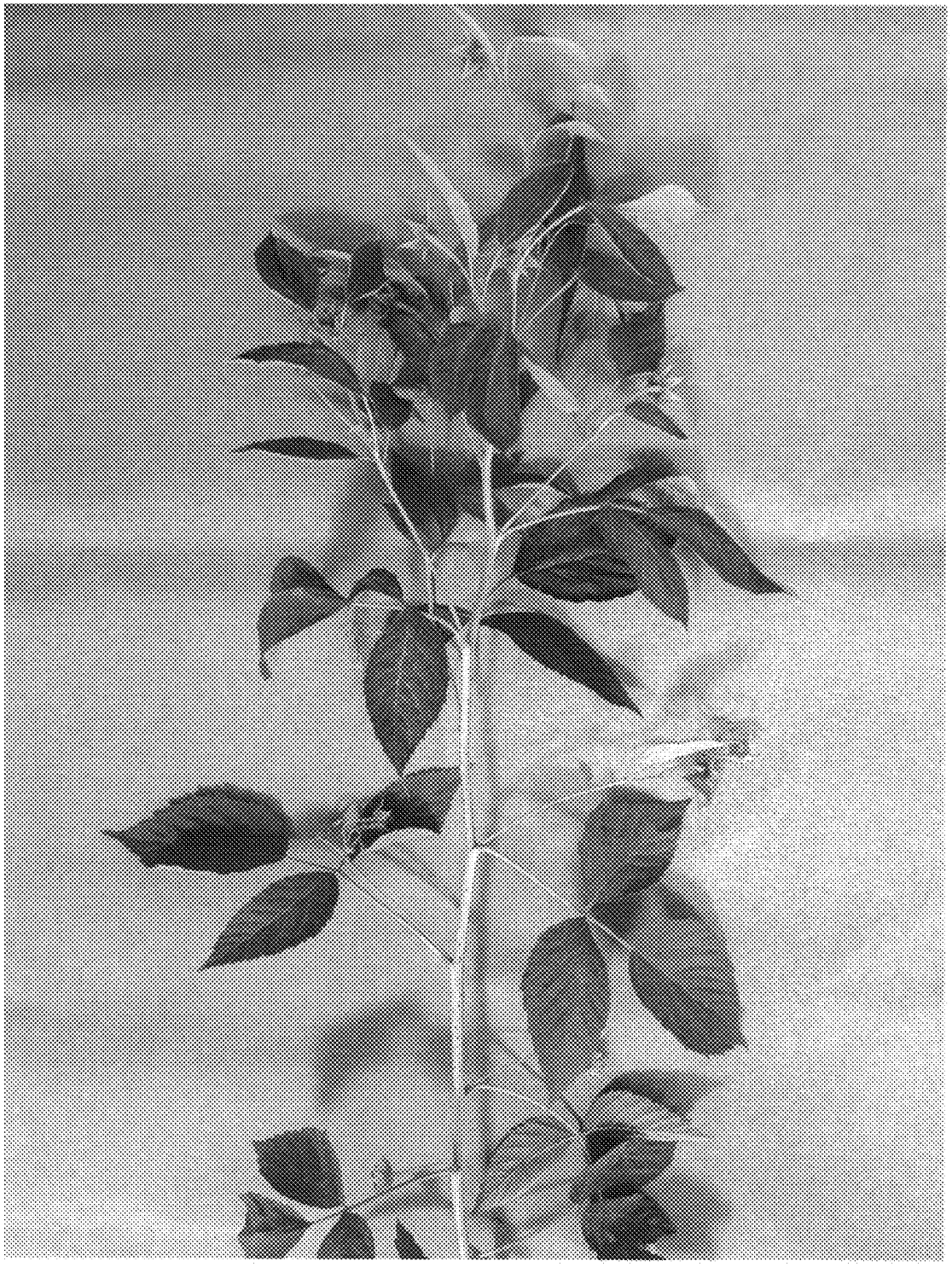
FIG. 4 illustrates a section of a plant of raspberry variety 'DrisRaspFifteen'.

The following descriptions set forth the distinctive characteristics of 'DrisRaspFifteen'. Unless where otherwise noted, the data that define these characteristics are based on observations taken from 'DrisRaspFifteen' plants that were one to two years old, grown in Santa Cruz County, Calif. from 2015 to 2018. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspFifteen' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.
*Botanical*.—*Rubus idaeus* L.
*Common name*.—Raspberry.
*Variety name*.—'DrisRaspFifteen'.

Parentage:

*Female parent*.—'RD335.8' (unpatented).
*Male parent*.—'Z367.1' (unpatented).

Plant:

*Height*.—190 cm.
*Width*.—140 cm.
*Length/width ratio*.—1.35.
*Growth habit*.—Arching.
*Primocane* (*current year's cane*).—Primocane color: RHS 132A (Dark Green). Cane length in autumn: 167 cm. Internodal distance at central ⅓ of cane: 6.5 cm. Anthocyanin coloration of cane: Absent.
*Very young shoot*.—Anthocyanin coloration of apex during rapid growth: Absent.
*Floricane* (*previous year's cane*).—Dormant cane color: RHS N200A (Brownish grey). Fruiting lateral attitude: Semi-erect.
*Prickles* (*spines*).—Length at 1 in height at end of harvest (from base to tip): 0.8 mm. Color: RHS 178A (Greyish Red).

Leaves:

*Predominant number of leaflets*.—Three.
*Profile of leaflets in cross section*.—Convex.
*Leaflet arrangement*.—Pinnately compound, free from overlapping.
*Color of upper side*.—RHS 132A (Strong Green).
*Color of underside*.—RHS 132C (Strong Green).
*Texture of upper side*.—Smooth.
*Texture of underside*.—Rugose.
*Venation pattern*.—Pinnate.
*Vein color*.—RHS 132D (Light Green).
*Terminal leaflet*.—Length: 149 mm. Width: 81. Length/width ratio: 1.85. Shape: Ovate. Apex shape: Truncate. Base shape: Obtuse. Margin: Serrate.

*Lateral leaflets*.—Length (basal pair): 133 mm. Width (basal pair): 63 mm. Length/width ratio (basal pair): 2.11. Relative position of lateral leaflets: Free. Shape: Elliptical. Apex shape: Truncate. Base shape: Cuneate to obtuse. Margin: Serrate.

*Rachis*.—Length between terminal leaflet and adjacent lateral leaflets: 42 mm. Diameter: 0.17 mm. Color: RHS 143C (Strong Yellow Green).

*Petiole*.—Length: 42 mm. Diameter: 0.19 mm. Color: RHS 143B (Strong Yellow Green).

Flowers:

*Diameter*.—22.93 mm.

*Depth*.—8.03 mm.

*Petal*.—Length: 8.30 mm. Width: 4.20 mm. Length/width ratio: 2.76. Number: 7.1. Shape: Oblong. Apex shape: Rounded. Base Shape: Cuneate to obtuse. Margin: Smooth. Color of upper side: RHS NN155B (White). Color of underside: RHS NN155A (Yellowish White).

*Sepal*.—Length: 9.08 mm. Width: 2.2 mm. Number: 5. Color of upper side: RHS 145B (Yellow Green). Color of underside: RHS 144B (Yellow Green).

*Pedicel*.—Length: 19.97 mm. Diameter: 0.94 mm. Color: RHS 141B (Strong Yellowish Green).

*Peduncle*.—Anthocyanin coloration: Absent. Length: 12 mm. Diameter: 1.2 mm. Color: RHS 141A (Deep Yellowish Green).

Fruit:

*Length*.—23.39 mm.

*Diameter*.—21.93 mm.

*Length/width ratio*.—1.07.

*General shape in lateral view*.—Conical.

*Color*.—RHS 42A (Vivid reddish orange).

*Number of drupelets per berry*.—120.

*Average weight per berry*.—6 g.

Production:

*Main bearing type*.—Both on floricane (previous year's cane) in summer and on primocane (current year's cane) in autumn.

*Primocane* (*current year's cane*).—Time of beginning of flowering: Early June. Time of beginning of fruit ripening: Late June. Length of fruiting period: Mid-July to late October. Yield: 23,800 kg to 41,800 kg of fruit per hectare per season from 7-month-old plants when grown in Watsonville, Calif.

*Floricane* (*previous year's cane*).—Time of vegetative bud burst: Early February. Time of beginning of flowering: Mid-March. Time of beginning of fruit ripening: Mid-April. Length of fruiting period: Mid-May to late July. Yield: 25,800 kg to 26,800 kg of fruit per hectare per season from 16-month-old plants when grown in Watsonville, Calif.

*Market use*.—Fresh Market.

COMPARISONS TO PARENTAL AND COMMERCIAL RASPBERRY VARIETIES

'DrisRaspFifteen' differs from the female parent 'RD335.8' (unpatented) in that fruit of 'DrisRaspFifteen' has a lighter color and an improved appearance when compared with fruit of 'RD335.8'.

'DrisRaspFifteen' differs from the male parent 'Z367.1' (unpatented) in that fruit of 'DrisRaspFifteen' has a larger size, a lighter color, and better shelf life when compared with fruit of 'Z367.1'.

'DrisRaspFifteen' differs from the commercial raspberry variety 'DrisRaspSix' (U.S. Plant Pat. No. 25,044) in that plants of 'DrisRaspFifteen' have an arching growth habit, whereas plants of 'DrisRaspSix' have a semi-erect growth habit. Moreover, 'DrisRaspFifteen' has a convex profile in cross section of leaflets and a free relative position of lateral leaflets, whereas 'DrisRaspSix' has a flat (straight) profile in cross section of leaflets and an overlapping relative position of lateral leaflets. Further, 'DrisRaspFifteen' has a conical fruit shape, whereas 'DrisRaspSix' has an ovate (broad conical) fruit shape.

'DrisRaspFifteen' differs from the commercial raspberry variety 'Driscoll Maravilla' (U.S. Plant Pat. No. 14,804) in that plants of 'DrisRaspFifteen' have an arching growth habit, whereas plants of 'Driscoll Maravilla' have a semi-erect growth habit. Moreover, 'DrisRaspFifteen' has predominantly three leaflets and a free relative position of lateral leaflets, whereas 'Driscoll Maravilla' has predominantly five leaflets and an overlapping relative position of lateral leaflets. Further, 'DrisRaspFifteen' has a conical fruit shape, whereas 'Driscoll Maravilla' has an ovate fruit shape. In addition, spines of 'DrisRaspFifteen' have a brownish purple color, whereas spines of 'Driscoll Maravilla' have a purple color.

What is claimed is:

1. A new and distinct variety of raspberry plant designated 'DrisRaspFifteen' as shown and described herein.

* * * * *